(12) United States Patent
Wagner

(10) Patent No.: US 6,849,061 B2
(45) Date of Patent: Feb. 1, 2005

(54) METHOD AND APPARATUS FOR PLEURAL DRAINAGE

(76) Inventor: Robert B. Wagner, 6228 Mazwood Rd., Rockville, MD (US) 20852

( * ) Notice: Subject to any disclaimer, the term of this patent is extended or adjusted under 35 U.S.C. 154(b) by 62 days.

(21) Appl. No.: 10/273,980

(22) Filed: Oct. 21, 2002

(65) Prior Publication Data

US 2004/0078026 A1 Apr. 22, 2004

(51) Int. Cl.⁷ .............................................. A61M 29/00
(52) U.S. Cl. ..................... 604/99.02; 604/912; 604/540
(58) Field of Search ................................ 604/916–919, 604/509, 907, 908, 912, 915, 920, 96.01, 97.01, 99.02, 540

(56) References Cited

U.S. PATENT DOCUMENTS

| | | | |
|---|---|---|---|
| 3,788,326 A | | 1/1974 | Jacobs .......................... 138/305 |
| 3,905,361 A | | 9/1975 | Hewson et al. ........... 128/145.5 |
| 3,993,080 A | * | 11/1976 | Loseff ........................... 604/28 |
| 4,327,720 A | * | 5/1982 | Bronson et al. ........ 128/207.15 |
| 4,543,089 A | * | 9/1985 | Moss ........................... 604/43 |
| 4,637,389 A | * | 1/1987 | Heyden ................. 128/207.15 |
| 4,642,092 A | * | 2/1987 | Moss ........................... 604/43 |
| 4,738,666 A | | 4/1988 | Fuqua ......................... 604/280 |
| 5,129,882 A | | 7/1992 | Weldon et al. ................ 604/96 |
| 5,135,474 A | | 8/1992 | Swan et al. ...................... 604/8 |
| 5,171,222 A | | 12/1992 | Euteneuer et al. .......... 604/102 |
| 5,275,616 A | | 1/1994 | Fowler ........................ 606/213 |
| 5,308,323 A | | 5/1994 | Sogawa et al. ................ 604/95 |
| 5,398,692 A | | 3/1995 | Hickey ........................ 128/673 |
| 5,486,195 A | | 1/1996 | Myers et al. ................ 606/213 |
| 5,616,126 A | * | 4/1997 | Malekmehr et al. ...... 604/96.01 |
| 5,653,230 A | * | 8/1997 | Ciaglia et al. ......... 128/207.15 |
| 5,669,380 A | * | 9/1997 | Garry et al. ........... 128/207.14 |
| 5,718,725 A | | 2/1998 | Sterman et al. ................ 623/2 |
| 5,785,686 A | * | 7/1998 | Runge ..................... 604/96.01 |
| 5,865,176 A | | 2/1999 | O'Neil .................. 128/207.15 |
| 5,910,128 A | * | 6/1999 | Quinn ..................... 604/93.01 |
| 6,010,479 A | * | 1/2000 | Dimitri .................... 604/96.01 |
| 6,500,145 B1 | * | 12/2002 | Bicakci et al. ........... 604/96.01 |
| 6,689,149 B2 | * | 2/2004 | Maahs ......................... 606/194 |
| 2001/0001957 A1 | * | 5/2001 | Allgeyer ................ 128/207.15 |
| 2002/0128597 A1 | * | 9/2002 | Grimes et al. ........... 604/96.01 |
| 2002/0173771 A1 | * | 11/2002 | Dono .......................... 604/540 |

OTHER PUBLICATIONS

Wagner et al., Highlights of the History of Nonpenetrating Chest Trauma, Thoracic Trauma, 1989, pp. 1–14.

* cited by examiner

Primary Examiner—Larry I. Schwartz
Assistant Examiner—M. G Bogart
(74) Attorney, Agent, or Firm—Blank Rome LLP

(57) ABSTRACT

Apparatus and method for evacuating material from a body cavity are disclosed. An elongated tubular member constructed and arranged to be inserted through an aperture in a patient's chest is provided. The tubular member is generally L-shaped and has a distal section and a proximal section. The distal section includes a plurality of openings for receiving air and liquids from within the patient's body. The proximal section receives and discharges air and liquids to a receiver. The proximal section includes an expandable cuff for positioning the tubular member in the patient's chest for preventing the plurality of openings from being obstructed in whole or in part.

20 Claims, 2 Drawing Sheets

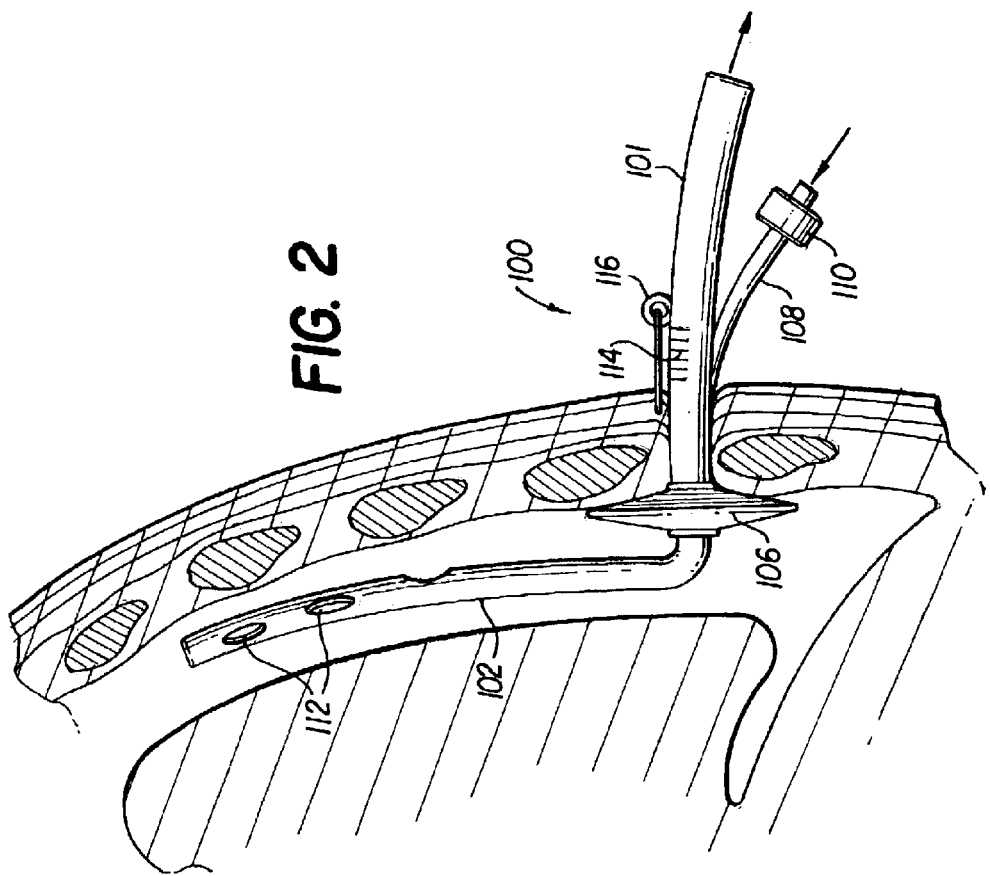
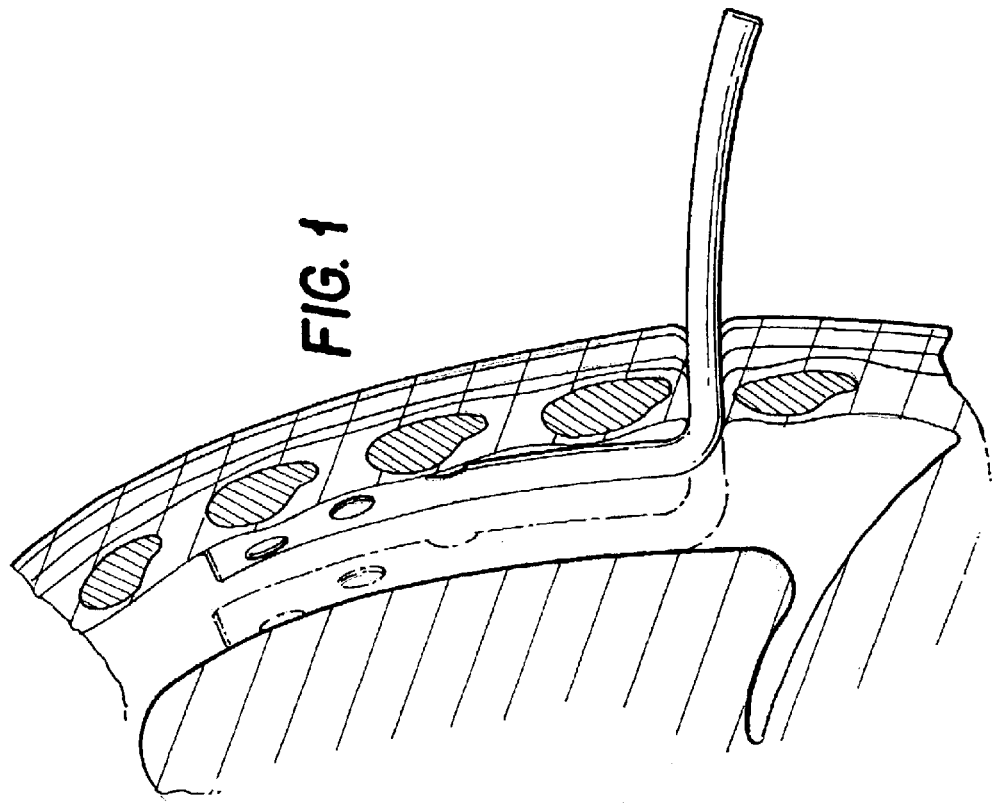

METHOD AND APPARATUS FOR PLEURAL DRAINAGE

BACKGROUND OF THE INVENTION

1. Field of the Invention

The invention relates to the evacuation of liquids and air from the pleural cavity in mammals. In particular, this invention relates to a chest tube and method for rapidly and accurately setting the chest tube in a patient in a medical emergency or trauma setting such that the tube performance is not impeded when inserted.

2. Background of the Invention

Thousands of cannulas or trocar catheters are inserted each year in patients suffering chest trauma brought on by incidents such as auto accidents, punctures and lung disease. These devices are used to evacuate air and liquids from the patient's pleural cavity, defined as that area of the human body between the neck and the diaphragm, partially encased by the ribs and containing the lungs. As is often the case in these situations, evacuation of materials is required immediately upon receiving a patient for treatment during an emergency and may be required for an extended period of time, for example during a patient's admittance to a hospital for treatment. To accomplish this, a practitioner experienced in setting chest tubes makes the necessary percutaneous penetration at an appropriate location on the patient's body and then inserts a flexible tube that contains small perforations or holes for receiving the material built up inside the patient's body. The material is then removed from the patient and discarded or otherwise processed. The chest tube is secured in place using a variety of methods common in the art including, but not limited to, adhesive tape, friction, suture with tether or tie lines.

A historical synopsis of the use of suction catheters, such as chest tubes, in general medical practice is disclosed in U.S. Pat. No. 4,738,666. As disclosed in that reference, the potential risk of infection from using chest tubes is outweighed by its benefits. However, passing a chest tube into a trauma patient's body so that the perforations at the distal end of the device are not partially blocked by a thoracic positioning between the lobes of a lung or having been placed between the chest wall and muscles, remains a challenge even to experienced emergency practitioners because it is a blind procedure. A misplaced chest tube results in a poorly functional or nonfunctioning tube due to partial blockage of the tube and a corresponding increase in hospitalization time and pain. Consequently, an improperly set chest tube reduces the medical benefits of the tube, possibly to the point where the risks are greater than the benefits of its use.

One method that has been frequently used to increase the efficiency of cannula and catheter tubes is to employ balloons. For example, prior to the conception of the present invention, dilation balloons attached to flexible tube cannulae have been employed for improving the efficiency of evacuation of fluids and solids. An apparatus for evacuating the stomach, as disclosed in U.S. Pat. No. 3,905,361, includes an elongated flexible tube with a perforated distal end for receiving stomach contents under vacuum, and an inflatable cuff balloon around the flexible tube for blocking the esophageal opening of the stomach to improve the vacuum. Similarly, an apparatus for assisting breathing, as disclosed in U.S. Pat. No. 3,788,326, includes a triple lumen flexible perforated catheter for use in a tracheal lumen to evacuate and supply air to the lungs, and an inflatable cuff balloon for positioning the tube in the trachea and increasing air flow through the tube.

In addition to the above uses, balloon catheters have been used in devices for blocking a blood vessel incision while an incision plug is set. Balloons have also been used extensively to extend or reposition a membrane within the patient's body. For example, in balloon angioplasty a double lumen apparatus containing an inflation lumen and an insertion lumen is inserted into a blood vessel and threaded forward to the location of a stenosis (restriction) where the balloon at the distal end of the device is inflated, forcing the blockage open. Often, the placement of a stent is accomplished at the same time to hold the vessel open. The balloon and stent are accurately placed because the operator can see the vessel and balloon using a special imaging system.

In still another use of balloons, a patient's heart atrial pressure has been measured by passing a nasal-gastric tube into the esophagus using a double lumen catheter with a dilation balloon and positioned adjacent to the left atrium of the patient's heart where the balloon is inflated to a set volume. The positioning of the balloon and catheter near the heart is accomplished either using an imaging system, an esophageal stethoscope or through trial and error by an experienced practitioner.

In still another use, a balloon catheter in which the balloon is employed at the distal end of a device is used to temporarily stop blood flow in a blood vessel. While the balloon is inflated, an optical fiber may be passed through the catheter to treat a lession or thrombi in the vessel with laser light, or an imaging fiber may be inserted to inspect the area of the lumen near the balloon where the blood flow has stopped.

While various configurations of the above balloon catheter/cannula devices have been used in the prior art, including devices with multiple lumens and multiple balloons, each of which may be inflated with air or liquids pumped from the proximate end of the device, and placed with assistance of imaging systems, none of the above devices or methods of using balloons have been employed with a chest tube to accurately set the chest tube inside a patient's thoracic region or other cavity to increase the effectiveness of evacuation.

What is needed, therefore, is an apparatus for the insertion of a chest tube in a proper position such that once it is inserted the tube is not partially blocked and a maximum volumetric flow rate is achieved. This can be accomplished, as in the present invention, using a dilation balloon or cuff attached to the chest tube to accurately position the tube inside the patient's thoracic cavity (or other cavity) and prevent it from resting on the inner chest wall or other membrane.

SUMMARY OF THE INVENTION

With respect to the aforementioned problems, it is therefore an object of the present invention to provide an apparatus and method for its use that overcomes the disadvantages of the prior art and is significantly more effective than previous devices or methods.

It is another object of the invention to increase the volumetric flow rate of air and liquid through a chest tube by preventing the blockage of the tube by improper positioning.

It is still another object of the invention to improve the setting of a chest tube so that a practitioner does not have to rely on an imaging system, or other visual techniques, or trial and error to locate the best position for the chest tube.

It is still another object of the invention to improve the accuracy of chest tube placement by inexperienced practitioners and even experienced practitioners when challenged by morbidly obese patients.

These and other objects of the present invention are achieved by providing an elongated L-shaped flexible tube with a dilation balloon that provides a structure that can be passed through a percutaneous penetration of a patient's body and is accurately positioned by inflating the balloon so that the perforated distal end of the structure is not blocked on any side.

One embodiment of the invention includes an apparatus for evacuating material from a body cavity, which includes an elongated tubular member constructed and arranged to be inserted through an aperture in a patient's chest, the tubular member being generally L-shaped and having a distal section and a proximal section, the distal section including a plurality of holes or perforations for receiving air and liquids from within the patient's body, and the proximal section receives and discharges air and liquids at the right angled turn to a receiver, the improvement of which includes an expandable cuff surrounding the proximal section for positioning the tubular member in the patient's chest for preventing the plurality of holes or perforations from being obstructed in whole or in part. inflating the cuff when the cuff is in operating position, an eyelet connected to the outer surface of the proximal section for securely attaching the tubular member to the patient, a valve attached to the inflation tube for regulating the flow of air or liquid into and out of the balloon, and a means for securing the valve in a closed position to prevent accidental positional changes of the tube.

Still other features of the apparatus include the balloon being fixedly attached to the proximal section, the distal section has a length of between 18 and 24 inches and an inside diameter of between 0.5 and 1 inch, and the outer surface of the proximal section includes markings for determining the position of the tubular member relative to the patient's body.

The objects of the present invention are also achieved by providing a method for evacuating material from a body cavity through an opening in the body, including the steps of receiving and positioning a patient for receiving a generally L-shaped tubular member; incising an opening in a patient large enough to advance the tubular member, the tubular member having a distal section and a proximal section, the distal section including a plurality of holes or perforations for receiving air and liquids from within the patient's body and an expandable cuff for positioning the tubular member to prevent obstruction of the plurality of holes or perforations; positioning the tubular member within the patient's body; and expanding the cuff to position the tubular member to prevent obstruction of the plurality of holes or perforations and its movement relative to the incised opening in the patient.

Other features of the method include the step of recording the position of the tubular member as indicated by markings on the proximal section; performing the steps of receiving, incising, positioning, expanding and recording in a trauma or emergency room setting; opening a valve on an inflation tube to cause air or liquid to enter a balloon under pressure thereby inflating the balloon, and securing the tubular member to the patient's chest using an eyelet attached to the proximal section.

These and other objects, advantages and features of the invention will become better understood from a detailed description of the preferred These and other objects, advantages and features of the invention will become better understood from a detailed description of the preferred embodiment of the invention which is described in conjunction with the accompanying drawings.

BRIEF DESCRIPTION OF THE DRAWINGS

FIG. 1 is a schematic of a traditional chest tube placement in a human being according to the prior art.

FIG. 2 is a schematic of a chest tube manufactured in accordance with the present invention with a balloon in the inflated position.

DETAILED DESCRIPTION OF THE INVENTION

Figure 3:
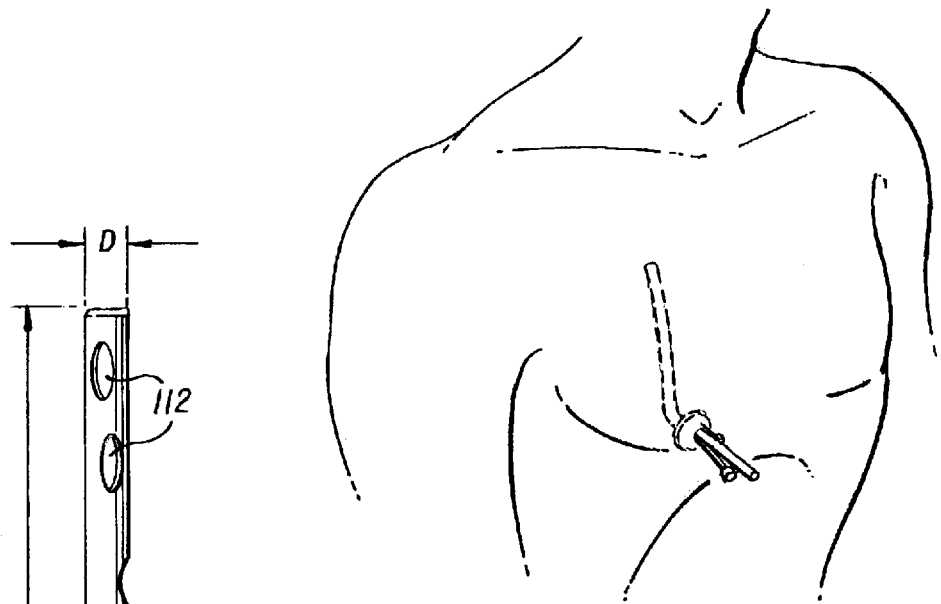
FIG. 3 is a schematic of a chest tube manufactured in accordance with the present invention and its use in a patient.

FIG. 1 is a schematic of a traditional chest tube and its placement inside the thoracic region of a patient through a percutaneous incision in the chest according to the prior art. As shown, the distal end of the chest tube, with its plurality of perforations for evacuating gases, liquids and solids, can easily rest against the structure of the ribs, if pulled forward, or pressed against the lungs, if pushed too far inward, reducing the volumetric flow rate of materials being evacuated. As shown in FIG. 1, a practitioner has a very small space in which set the chest tube to maximize the efficiency of the device.

FIG. 2 is a schematic of a chest tube 100, manufactured in accordance with the present invention, that is placed inside the thoracic cavity of a patient through a percutaneous incision in the patient's chest. The chest tube 100 is generally L-shaped, having a distal section 102 for receiving fluid, a proximal section 104 for the carrying of the fluid outwardly from the chest. The proximal section 104 includes a balloon 106 (shown inflated), which communicates with an inflation tube 108 connected to a pump (not shown) or other source of air or liquid pressure. Eyelet 116, for securing the tube in place, is provided on the surface of the proximal section 104. Those skilled in the prior art will recognize that alternative methods of securing the tube to the patient may be used, including, but not limited to, adhesive tape, friction and mechanical locking. The distal section 102 includes a plurality of holes or perforations 112 for receiving fluids and other materials in the chest cavity. Also, graduations are marked on the outer surface of the proximal section 104 to assist in accurately placing the tube and for ensuring the tube has not been repositioned over time.

The distal section 102 and proximal section 104 may be made from any suitable material, as for example, polyolefin, nylon, TEFLON®, or polycarbonate. It will be obvious to one of skill in the art that the material must be sufficiently rigid to maintain the distal section 102 in a correct position, but flexible enough to move when displaced to prevent further injury to the patient. Likewise, the balloon 106 may be made from any suitable material, including polyolefin, polyethylene, polyvinyl chloride, and natural or synthetic rubber that is expandable, resilient, and is capable of being cleaned by conventional disinfecting methods without compromising its physical properties.

FIG. 3 is a schematic of the chest tube 100 manufactured in accordance with the present invention and its use in a patient. The device may be inserted in a patient that is positioned vertically or, in most cases, in a prone position. The device is inserted after a percutaneous incision is made in the patient's chest with a scalpel or by using a trocar to puncture the chest.

Figure 4:
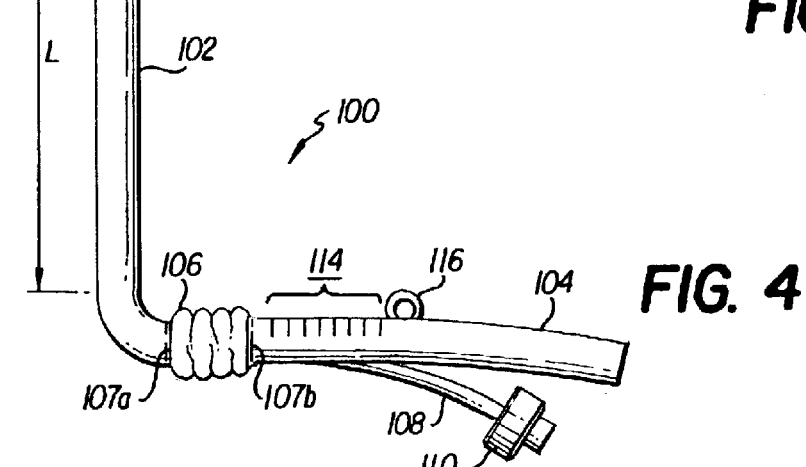
FIG. 4 is a schematic of a chest tube manufactured in accordance with the present invention.

FIG. 4 is a schematic of the chest tube 100 manufactured in accordance with the present invention. As shown, the distal section 102 may be any length L, however, in most instances the length will be approximately 18 to 24 inches. The distal section 102 may be any diameter, D, however, in most instances the inside diameter will be approximately 0.25-inch to about 1-inch, the diameter limited primarily by the intra-skeletal distance between the patient's ribs. The proximal section 104, including the inflation tube 108, may be any length but will necessarily be long enough to accommodate various size patients and to allow room for connections to a syringe (not shown).

As shown in FIG. 4, the distal section 102 contains a plurality of holes or perforations 112 for receiving fluids in the chest cavity. The holes or perforations 112 may be any size but should not be too large that the structural rigidity of the tube is compromised. Also, the holes or perforations 112 may be any shape, such as round, elliptical or rectangular. However, they should be manufactured in such a way as to maximize volumetric flow. Moreover, the edges are smooth and free from burrs or cracks to prevent buildup of material.

Also shown in FIG. 4 is the balloon 106 in the deflated position. As shown in this embodiment, the balloon 106 is securely attached to the outer circumference of the proximal section 104 at fixed collar points 107a and 107b. When deflated, the balloon 106 is gathered close to the proximal section 104 to allow insertion of the device into the patient's thoracic cavity with minimal resistance from the balloon.

Also shown in FIG. 4 are gradient markings 114 on the outer surface of proximal section 104. The markings may indicate any distance in English or metric units, spaced evenly apart or otherwise, and extend the entire length or a fraction of the length of the proximal section 104, as shown. The markings may be used, for instance, by practitioners to record the position of the tube when it is inserted to ensure the tube has not shifted over time.

Also as shown in FIG. 4, the inflation tube 108 extends from the proximal section 104 at a point near the proximal end of the balloon 106. The diameter of the distal section 102 at any portion within the patient's body is constant. The diameter of the chest tube 100 within the chest wall may be slightly larger or the same as the diameter of the distal section 102 of the tube. Where the inflation tube 108 extends away from the proximal section 104, the diameter will be slightly larger.

The inflation tube 108 contains a check valve 110, as shown in FIG. 4, for maintaining pressure inside the balloon 106 when it is inflated. The valve may be made from any suitable material including stainless steel, plastic or combinations a safety feature to prevent accidental activation and deflation of the balloon 106.

Figure 5:
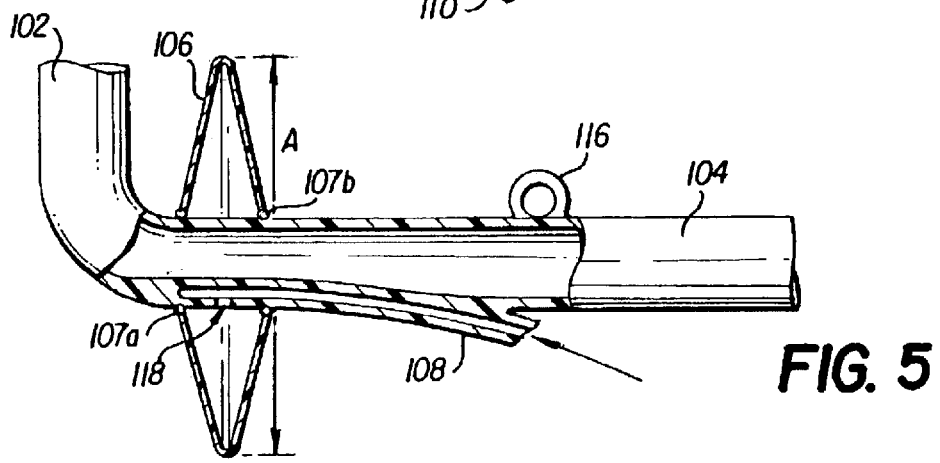
FIG. 5 is a cross section view of a chest tube manufactured in accordance with the present invention with a balloon in the inflated position.

FIG. 5 is a cross section view of the chest tube 100 manufactured in accordance with the present invention with the balloon 106 in the inflated position. In the embodiment of FIG. 5, air or liquid is used to pressurize the balloon 106 and is introduced into the balloon via inflation tube 108 through one or more apertures 118.

In use, the method according to the present invention includes the steps of positioning a patient to be treated, inserting the distal section 102 of the chest tube 100 and the balloon 106 into the patient's chest, connecting the proximal section 104 to a receiving container (which may also include a suction device), inflating the balloon 106, and properly positioning the chest tube 100. If required, a discharge pump is then started and fluid is evacuated from the patient's chest. It is to be understood that the invention is not limited to the exact details of construction, operation, exact materials or embodiments shown and described above, as obvious modifications and equivalents will be apparent to one skilled in the art.

I claim:

1. An apparatus for evacuating material from a body cavity in a patient's chest, comprising:
    an elongated tubular member constructed and arranged to be inserted through an aperture in the patient's chest, said tubular member being generally L-shaped and having a distal section and a proximal section, said distal section including a plurality of openings for receiving material from within the body cavity, and said proximal section receives and discharges the material to a receiver, said proximal section including an expandable cuff for positioning said distal section of said tubular member in the body cavity of the patient's chest for preventing said plurality of holes or perforations from being obstructed in whole or in part, wherein said tubular member is generally L-shaped when said expandable cuff is not expanded, and said tubular member is sufficiently rigid to maintain said distal section in a desired non-obstructing position within the body cavity when the cuff is expanded.

2. The apparatus of claim 1, wherein said expandable cuff is a fluid inflatable balloon which surrounds said proximal section; and further including a tube communicating with said cuff for inflating said cuff when said cuff is in an operating position.

3. The apparatus of claim 1, further comprising an eyelet connected to the outer surface of said proximal section for securely attaching said tubular member to the patient.

4. The apparatus of claim 2, further comprising an eyelet connected to the outer surface of said proximal section for securely attaching said tubular member to the patient.

5. The apparatus of claim 2, further comprising a valve attached to said inflation tube for regulating the flow of air or liquid into and out of said balloon.

6. The apparatus of claim 5, wherein said valve comprises a means for securing said valve in a closed position to prevent accidental pressure changes within said balloon.

7. The apparatus of claim 2, wherein one end of said balloon is secured to the outer surface of said proximal section.

8. The apparatus of claim 2, wherein said balloon is fixably connected to the outer surface of said proximal section.

9. The apparatus of claim 1, wherein the outer surface of said proximal section includes markings for determining the position of said tubular member relative to the patient's body.

10. The apparatus of claim 2, wherein the outer surface of said proximal section includes markings for determining the position of said tubular member relative to the patient's body.

11. The apparatus of claim 1, wherein said tubular member is sufficiently flexible to be displaced by an obstruction in the body cavity.

12. The apparatus of claim 1, wherein said expandable cuff displaces said distal section of said tubular member within the body cavity.

13. The apparatus of claim 1, wherein said cuff is symmetrical in shape.

14. The apparatus of claim 1, wherein the cuff positions the distal section in the desired non-obstructing position when the cuff is expanded and positioned against a wall of the body cavity.

15. A method for evacuating material from a body cavity in a patient's chest through an opening in the body, comprising the steps of:

receiving and positioning a patient for receiving a generally L-shaped tubular member, said tubular member having a distal section and a proximal section and an expandable cuff for positioning said tubular member within the body cavity, wherein said tubular member is generally L-shaped when the expandable cuff is not expanded;

incising an opening in a patient's chest and advancing said tubular member into the body cavity through the opening, wherein said distal section of said tubular member includes a plurality of openings for receiving material from within the body cavity;

positioning said tubular member within the body cavity; and expanding said cuff to position said tubular member within the body cavity to prevent obstruction of said plurality of openings.

16. The method of claim 15, further comprising the step of recording the position of said tubular member as indicated by markings on said proximal section.

17. The method of claim 16, wherein said step of expanding comprises expanding said cuff and positioning said cuff against a wall of the body cavity to position the distal section of said tubular member within the body cavity to prevent obstruction of said plurality of openings.

18. The method of claim 15, wherein said expandable cuff is a balloon which surrounds said tubular member and which communicates with an inflation tube, said method further including opening a valve on said inflation tube to cause air or liquid to enter said balloon under pressure thereby inflating said balloon.

19. The method of claim 15, further comprising an eyelet connected to the outer surface of said proximal section, said method further including securing said tubular member to the patient with a line connected between said eyelet and the patient's body.

20. The method of claim 15, wherein said cuff is symmetrical in shape.

* * * * *